United States Patent [19]
Meiwes et al.

[11] Patent Number: 5,641,659
[45] Date of Patent: Jun. 24, 1997

[54] α-L-RHAMNOSIDASE FOR OBTAINING RHAMNOSE, A PROCESS FOR ITS PREPARATION AND ITS USE

[75] Inventors: Johannes Meiwes, Idstein/Ts; Dieter Wullbrandt, Hofheim/Taunus; Carlo Giani, Frankfurt am Main, all of Germany

[73] Assignee: Hoechst Aktiengesellschaft, Frankfurt am Main, Germany

[21] Appl. No.: 465,414

[22] Filed: Jun. 5, 1995

Related U.S. Application Data

[62] Division of Ser. No. 156,718, Nov. 24, 1993, Pat. No. 5,468,625.

[30]  Foreign Application Priority Data

Nov. 27, 1992 [DE] Germany ............... 42 39 859.2

[51] Int. Cl.$^6$ ................ C12P 19/02; C12N 1/14; C12N 9/24; C12N 9/26
[52] U.S. Cl. ............... 435/105; 435/71.1; 435/201; 435/209; 435/210; 435/256.3; 435/933
[58] Field of Search ............... 435/71.1, 105, 435/201, 209, 210, 256.3, 933

[56]  References Cited

U.S. PATENT DOCUMENTS

| | | | |
|---|---|---|---|
| 4,758,283 | 7/1988 | Takemura et al. | 127/36 |
| 4,772,334 | 9/1988 | Hatanaka et al. | 127/36 |
| 4,933,281 | 6/1990 | Daniels et al. | 435/101 |
| 4,971,812 | 11/1990 | Tsen | 426/51 |
| 5,008,381 | 4/1991 | Kratky et al. | 536/124 |
| 5,077,206 | 12/1991 | Cheetham et al. | 435/105 |
| 5,468,625 | 11/1995 | Meiwes et al. | 435/105 |

FOREIGN PATENT DOCUMENTS 0 317 033  5/1989  European Pat. Off. .

OTHER PUBLICATIONS

Gabor et al. "Daten zur charakterisierung von Naringinase aus Penicillium species," Hoppe Seyler z. Physiol. Chem., Bd. 365, No. 9 (1984) p. 914.

Abstract No. 159152w, "Manufacture of Thermostable hesperidinase AH-2." Chemical Abstracts, vol. 98, No. 19 (May 1983) p. 387.

*Primary Examiner*—Herbert J. Lilling
*Attorney, Agent, or Firm*—Finnegan, Henderson, Farabow, Garrett & Dunner, L.L.P.

[57]  ABSTRACT

The invention relates to α-L-rhamnosidase, which catalyzes the cleavage of the bond between terminal rhamnose and the aglycone of rhamnose-containing glycosides, a process for preparing it by biotechnological means, and its use for preparing L(+)-rhamnose (6-deoxy-L-mannose).

16 Claims, No Drawings

SEQUENCE LISTING ( 1 ) GENERAL INFORMATION:

( i i i ) NUMBER OF SEQUENCES: 3

( 2 ) INFORMATION FOR SEQ ID NO:1:

( i ) SEQUENCE CHARACTERISTICS:
        ( A ) LENGTH: 22 amino acids
        ( B ) TYPE: amino acid
        ( D ) TOPOLOGY: linear ( i i ) MOLECULE TYPE: peptide ( x i ) SEQUENCE DESCRIPTION: SEQ ID NO:1:

Asp Thr Asn Asp Gln Thr Ser Ala Lys Val Asp Arg Gly Thr Phe Asp
    1                      5                                10                      15

Asp Pro Ala Ala Arg Leu
                              20

( 2 ) INFORMATION FOR SEQ ID NO:2:

( i ) SEQUENCE CHARACTERISTICS:
        ( A ) LENGTH: 23 amino acids
        ( B ) TYPE: amino acid
        ( D ) TOPOLOGY: linear ( i i ) MOLECULE TYPE: peptide ( i x ) FEATURE:
        ( A ) NAME/KEY: Region
        ( B ) LOCATION: 5
        ( D ) OTHER INFORMATION: /note= "Xaa is probably cysteine."

( i x ) FEATURE:
        ( A ) NAME/KEY: Region
        ( B ) LOCATION: 22
        ( D ) OTHER INFORMATION: /note= "Xaa is an undetermined
            amino acid."

( x i ) SEQUENCE DESCRIPTION: SEQ ID NO:2:

Phe Phe Gly Ser Xaa Gln Ser Leu Tyr Leu Lys Leu Val Leu Lys Phe
    1                      5                                10                      15

Gly Thr Leu Phe Asp Xaa Ala
                              20

( 2 ) INFORMATION FOR SEQ ID NO:3:

( i ) SEQUENCE CHARACTERISTICS:
        ( A ) LENGTH: 20 amino acids
        ( B ) TYPE: amino acid

```
        ( D ) TOPOLOGY: linear ( i i ) MOLECULE TYPE: peptide ( i x ) FEATURE:
        ( A ) NAME/KEY: Region
        ( B ) LOCATION: 5
        ( D ) OTHER INFORMATION: /note= "Xaa is an undetermined
                amino acid."

( i x ) FEATURE:
        ( A ) NAME/KEY: Region
        ( B ) LOCATION: 8
        ( D ) OTHER INFORMATION: /note= "Xaa is an undetermined
                amino acid."

( x i ) SEQUENCE DESCRIPTION: SEQ ID NO:3:

Ala  Ser  Val  Pro  Xaa  Gly  Glu  Xaa  Ile  Leu  Ala  Pro  Ser  Ser  Ile  Glu
 1               5                        10                         15

Leu  Ile  Pro  Thr
           20
```

α-L-RHAMNOSIDASE FOR OBTAINING RHAMNOSE, A PROCESS FOR ITS PREPARATION AND ITS USE

This is a division of application Ser. No. 08/156,718, filed Nov. 24, 1993 now U.S. Pat. No. 5,468,625.

The invention relates to α-L-rhamnosidase, which catalyzes the cleavage of the bond between terminal L(+)-rhamnose and the aglycone of rhamnose-containing glycosides, to a process for its preparation by biotechnological means, and to its use for preparing L(+)-rhamnose (6-deoxy-L-mannose). In that which follows, this latter sugar is designated L-rhamnose.

L-Rhamnose is very well suited for use as a chiral structural component for the preparation of different organic compounds. L-Rhamnose or its derivatives are being used to an ever increasing extent in the synthesis of pharmaceutical products and plant protection agents, as well as in the spheres of plant and animal cytology, microbiology, immunobiology and the preparation of fragrances. Thus, using L-rhamnose as the starting compound, 2,5-dimethyl-4-hydroxy-2,3-dihydrofuran-3-one (Furaneol®) can, for example, be prepared, which, in turn, is used as the parent substance for various fragrant substances in the foodstuffs and perfume industries.

L-Rhamnose can only be obtained with very great difficulty by the chemical route. It can, however, be isolated extractively from various natural sources, for example from the flavone glycosides hesperidin, rutin, naringin and quercitrin, or, for example, from gum arabic or marine algae, following acid hydrolysis. [Biotechnology and Bioengineering, Vol. 33, p. 365 (1989), R. J. Linhardt et al.; EP-A-0 317 033; JPA 62293]. Disadvantages of these processes are the elaborate steps for isolating L-rhamnose, some of which involve using organic solvents and, in addition, the aromatic, potentially toxic by-products accruing during the working up, and the constituents of the natural sources, which constituents fluctuate in composition in dependence on the seasonal rhythm.

L-Rhamnose can also be prepared in the form of rhamnose-containing heteropolysaccharides by fermentation using bacteria of different genera, such as, for example, Alcaligenes, Acinetobacter, Klebsiella, Streptococcus or Lactobacillus. [Enzyme Microb. Technol., Vol. 10, p. 198 (1988), M. Graber et al.; J. Amer. Chem. Soc., Vol. 71, p. 4124 (1945), F. G. Jarvis and M. J. Johnson; J. Bacteriol., Vol. 68, p. 645 (1954), G. Hauser and M. L. Karnovsky].

Disadvantages of these processes are the customarily low yields, conditioned by viscosity, and the necessary separation of L-rhamnose from a fixture of different sugars following hydrolytic cleavage of the hetero-polysaccharide.

Numerous publications and patents deal with the production of rhamnolipids by means of fermentation using Pseudomonas aeruginosa. [Applied and Environmental Microbiology, Vol. 51, p. 985 (1986), H. E. Reiling et al.; J. Chem. Techn. Biotechnol., Vol. 45, p. 249 (1989), K. Venkata Ramana et al.; U.S. Pat. No. 4,933,281, Daniels et al.; German Published Patent Application 2 150 375, 1972; U.S. Pat. No. 4,814,272, Wagner et al.]

In principle, four rhamnolipids (RL1–RL4, see FIG. 1) are present in the microorganism culture solution, which rhamnolipids are composed of one or two L(+)-rhamnose units and one or two β-hydroxydecanoic acids. [Z. Naturforsch. 40 c, p. 61 (1985), C. Syldatk et al.]. Rhamnolipids 1 and 3 are quantitatively the most important.

FIG. 1: Rhamnolipids from microorganisms

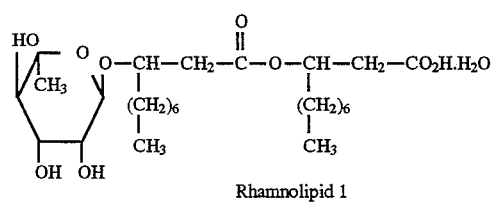

Rhamnolipid 1

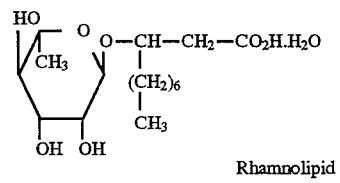

Rhamnolipid 2

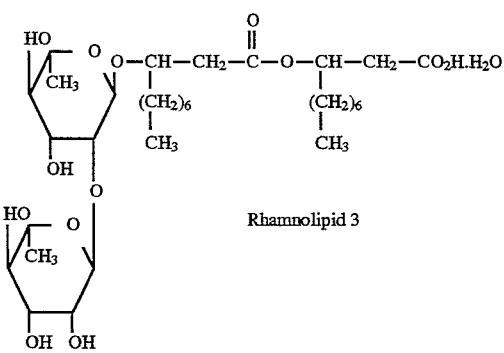

Rhamnolipid 3

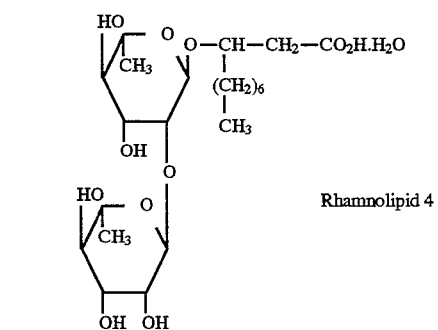

Rhamnolipid 4

In addition, it is known to obtain L-rhamnose from flavone glycosides, rhamnolipids or oligosaccharides by enzymic cleavage using the soluble or immobilized α-L-rhamnosidases naringinase and hesperidinase. [U.S. Pat. No. 5,077,206; Eur. Pat. 88202595.0; Turecek, P. and Pittner, F., Appl. Biochem. and Biotech. 13, 1–13 (1986)]. Naringinase and hesperidinase have in each case a molecular weight of about 90 kd and were isolated from Penicillium decumbens and Aspergillus niger, respectively.

Naringinase and hesperidinase catalyze the cleavage of the bond between two monosaccharides, chiefly the elimination of terminal rhamnose from flavanone glycosides, such as, for example, from hesperidin and naringin, or from rhamnolipid 3 or 4.

Naringinase and hesperidinase catalyze the cleavage of the bond between terminal rhamnose and an aglycone in rhamnose-containing glycosides appreciably more slowly (factor: 10–100; see Example 1).

The consequence of this is that a very long period of time is required in order to completely cleave rhamnose from the rhamnolipid 1–4 mixture, since the rhamnolipids 1 and 3 which are present to the greatest extent quantitatively in the microorganism culture solution are composed of L-rhamnose and aglycone (fatty acid).

α-L-Rhamnosidase has now been isolated, surprisingly, from Penicillium sp. which catalyzes the cleavage of the bond between terminal L-rhamnose and the aglycone of rhamnose-containing glycosides, i.e. which has the opposite specificity to the known α-L-rhamnosidases naringinase and hesperidinase.

The invention thus relates to
1. α-L-rhamnosidase, which can be obtained
    by fermenting Penicillium sp. DSM 6825 and/or 6826 separating off the biomass from the culture broth, and concentrating the culture supernatant.
2. α-L-Rhamnosidase having a molecular weight of 60–100 kd, which α-L-rhamnosidase contains the amino-terminal amino acid sequence

D-T-N-D-Q-T-S-A-K-V-D-R-G-T-F-D-D-P-A-A-R-L (SEQ ID NO:1)

or

F-F-G-S-X-Q-S-L-Y-L-K-L-V-L-K-F-G-T-L-F-D-X-A (SEQ ID NO:2)

and catalyzes the cleavage of the bond between terminal L-rhamnose and the aglycone of rhamnose-containing glycosides.
3. A process for preparing α-L-rhamnosidase, wherein Penicillium sp. is cultivated in a nutrient medium until α-L-rhamnosidase accumulates in the culture, the biomass is then separated off from the culture broth, and the culture supernatant thus obtained is concentrated.
4. A use of α-L-rhamnosidase for the preparation of L-rhamnose.
5. Penicillium sp. DSM 6825
6. Penicillium sp. DSM 6826.

The invention is described in detail below, in particular in its preferred embodiments.

The compound L(+)-rhamnose (=6-deoxy-L-mannose) is designated L-rhamnose.

A compound, or the moiety of a compound, which does not contain any sugar is designated an aglycone. In this invention, fatty acid compounds or flavone compounds, in particular, are designated aglycones.

The following abbreviations, which correspond to the single letter code known from the specialist literature, are used for the amino acids.

| Amino acid | Abbreviations | Letter code |
|---|---|---|
| Glycine | Gly | G |
| L-alanine | Ala | A |
| L-valine | Val | V |
| L-leucine | Leu | L |
| L-isoleucine | Ile | I |
| L-phenylalanine | Phe | F |
| L-proline | Pro | P |
| L-serine | Ser | S |
| L-threonine | Thr | T |
| L-cysteine | Cys | C |
| L-methionine | Met | M |
| L-tryptophan | Trp | W |
| L-Tyrosine | Tyr | Y |
| L-asparagine | Asn | N |

-continued

| Amino acid | Abbreviations | Letter code |
|---|---|---|
| L-glutamine | Gln | Q |
| L-asparaginic acid | Asp | D |
| L-glutamic acid | Glu | E |
| L-lysine | Lys | K |
| L-arginine | Arg | R |
| L-histidine | His | H |

α-L-Rhamnosidase can be isolated from the culture broth both in small quantities (up to 1 gram) and in large quantities ($\leq 1$ kg), since the preparation process can be carried out on a laboratory scale (fermentation of the microorganisms in volumes up to 1 liter) and on an industrial scale (fermentation of the microorganisms on a cubic meter scale).

The molecular weight of the α-L-rhamnosidase according to the invention is determined by means of SDS gel electrophoresis (SDS=sodium dodecyl sulfate) and by means of gel chromatography. This method of gel chromatography is described, for example, in Molecular Biology of the Cell, Bruce Alberts et al., Garland Publishing, Inc. New York & London, 3rd Edition, 1983, pp. 174, 265–266.

The abbreviation "IEP"0 stands for "isoelectric point" and is defined as the pH at which the net charge on the protein, or in the present case the enzyme, is zero. The IEP is determined by means of chromatofocussing.

Penicillium sp. was isolated from a compost composed of garden waste in 6232 Bad Soden, Germany. The microorganism was isolated and purified in accordance with processes known to the person skilled in the art by culture dilution and plating out on selective agar. For example, the compost sample can be suspended in 0.9% strength sodium chloride solution and an enrichment culture of this suspension can be set up in selective medium containing rhamnolipids and/or rhamnolipid derivatives, preferably $C_1$–$C_{18}$-alkyl esters of rhamnolipid-2 as the sole carbon source. $C_1$–$C_4$-Alkyl esters of rhamnolipid-2, such as, for example, methyl rhamnolipid-2 or tert-butyl rhamnolipid-2, are used with particular preference as the carbon source.

Formulae

Rhamnolipid 2 tert-butyl ester

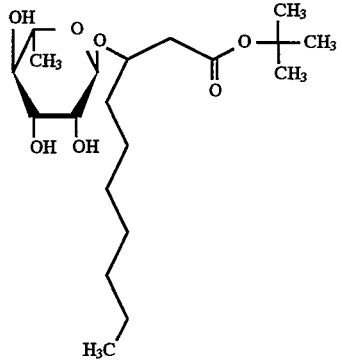

-continued
Formulae

Rhamnolipid 2 methyl ester

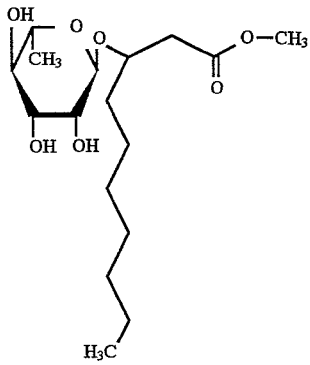

Penicillium sp. DSM 6825 and DSM 6826 have the following morphological characteristics (after R. A. Samson et al., Introduction to Food-borne Fungi, Institute of the Royal Netherlands Academy of Arts and Sciences, 3rd Edition, 1988):

Penicillium sp. DSM 6825

| Branching of the conidia | monoverticillate |
|---|---|
| Phialides | ampulliform |
| Conidia | spiny |

Penicillium sp. DSM 6826

| Branching of the conidia | biverticillate |
|---|---|
| Phialides | flask-shaped |
| Conidia | warty |

Penicillium sp. DSM 6825 and 6826 may be fermented together or separately.

Insofar as they produce the enzyme α-L-rhamnosidase, mutants and variants can also be employed instead of the isolate DSM 6825 and/or 6826. Such mutants can be produced, in a manner known per se, by physical means, for example irradiation, such as using ultraviolet or X-rays, or with chemical mutagens, such as, for example ethyl methanesulfonate (EMS), 2-hydroxy-4-methoxybenzophenone (MOB) or N-methyl-N'-nitro-N-nitrosoguanidine (MNNG). The process for preparing the abovementioned α-L-rhamnosidases is as follows:

Following isolation and purification of Penicillium sp. by repeated passage of the mixed culture of the resulting microorganisms in selective medium, an enrichment of the microorganisms which produce the enzyme according to the invention is achieved.

The microorganisms thus obtained are plated out on agar plates (selective medium) in order to obtain pure cultures from the mixed culture.

The pure cultures are replicated and tested for their ability to form the enzyme according to the invention.

It is found that microorganisms of the genus Penicillium sp. form the enzyme according to the invention. The fungal genus is determined with the aid of morphological, taxonomic and biochemical criteria in accordance with methods known to the person skilled in the art. The color of the colonies is green.

The investigations of the ability of the Penicillium sp. colonies to form the enzyme according to the invention lead to the isolation of two strains which are notable for a particularly high level of production of α-L-rhamnosidase. These two strains are: Penicillium sp. DSM 6825 and DSM 6826.

In accordance with the rules of the Budapest Treaty, these strains were deposited with the Deutschen Sammlung von Mikroorganismen und Zellkulturen GmbH (German Collection of Microorganisms and Cell Cultures), Mascheroder Weg 1B, 3400 Braunschweig, Germany, on the 29th Nov. 1991 under the numbers: Penicillium sp. DSM 6825 and 6826.

The microorganisms concerned are cultivated under the conditions which are customary for Penicillium sp. Accordingly, cultivation is effected on complex or defined media; preferably, the media contain yeast extract, casamino acids, corn steep, meat extract, peptone, caseine, gelatin, tryptone, nitrate, ammonium or urea as the nitrogen source, and starch, dextrin, sucrose, glucose, glycerol and malt extract as the carbon source.

Magnesium, calcium, sodium, potassium, iron, zinc, cobalt or phosphate can be employed as further components. The use of rhamnolipids or their alkyl esters (crude mixtures or purified rhamnolipids) as the C source, alone or in combination with additional C sources, is found to be particularly suitable.

The cultivation is effected at 27° C. over a period of 72–120 hr. Isolation of the α-L-rhamnosidase according to the invention, which may be necessary, is effected in a customary manner, e.g. by filtration or centrifugation to separate off the biomass, the α-L-rhamnosidase for the most part being located in the supernatant.

The supernatant can be concentrated by ultrafiltration and then lyophilized. Further purification steps, such as, for example, precipitations, anion exchange chromatography, chromatofocussing, HIC chromatography (hydrophobic interaction chromatography), exclusion chromatography and affinity chromatography, may be carried out, depending on the degree of enzyme purity desired.

Preferably, the purification is effected by filtering to separate off the biomass, subsequent ultrafiltration to concentrate the enzyme in the remaining supernatant, then anion exchange chromatography followed by chromatofocussing, and finally exclusion chromatography.

The α-L-rhamnosidase according to the invention has a molecular weight of 60–100 kD, depending on the degree of glycosylation, and an isoelectric point of 5.6–5.8. The pH optimum for the cleavage of p-nitrophenyl-α-L-rhamnopyranoside is 5.0–5.5 and the temperature optimum is 50°–55° C.

The amino-terminal sequence of the α-L-rhamnosidase from the strain Penicillium sp. DSM 6826 and of naringinase is in principle determined in accordance with the Edman process, which is known from the literature. For this purpose, amino acid chains are mixed with phenyl isothiocyanate under suitable conditions. The chemical compound preferentially attaches itself to the free amino-terminal amino group. In the presence of anhydrous acid, the end-terminal amino acid is eliminated as a carbamyl derivative. This compound is investigated in order to identify the amino-terminal amino acid. The remainder of the amino acid chain (which now lacks the initial amino acid) can now be subjected to renewed treatment with phenyl isothiocyanate to determine the next amino acid in order, etc. In principle, this procedure can be carried out many times stepwise in succession so that the total amino acid frequency of the chain can be deduced. In the present case, in addition to this, the N-terminal amino acid sequencing is carried out using a gas phase sequencer (type 477 A from Applied Biosystems) and the amino acid analysis using an on-line amino acid analyzer (type 130 A PTC analyzer from Applied Biosystems). The methods are published in FEBS Letters, Vol. 292, pp. 405–409, 1991.

It was possible to elucidate the following amino-terminal constituent sequence of the α-L-rhamnosidase:

D-T-N-D-Q-T-S -A-K-V-D-R-G-T-F-D-D-P -A-
A-R-L     (SEQ ID NO: 1)

or

F-F-G-S-X-Q-S-L-Y-L-K-L-V-L-K-F-G-T-L-F-
D-X-A     (SEQ ID NO: 2)

The α-L-rhamnosidase according to the invention can be employed in free or in immobilized form, where, in the latter case, all current methods of immobilization are suitable. Silica gel, for reasons of economy, can, for example, be used as the support.

The α-L-rhamnosidase catalyzes the cleavage of the bond between the terminal L-rhamnose and the aglycone of rhamnose-containing glycosides and is thus suitable for preparing rhamnose.

The cleavage is carried out in aqueous solutions which are buffered or not buffered. Aqueous solutions are, for example, the culture broth of the microorganism (no buffering necessary) or distilled water. In the latter case, a buffering with phosphate or Tris buffer, preferably ammonium acetate buffer, is necessary (concentration of the buffer: 5–100 mM, preferably 10–50 mM). The pH of the aqueous solution is pH 3.5–8, preferably pH 5–6. The temperature which is necessary for the enzyme activity is between 4° C.–65° C., preferably 45° C.–55° C. The reaction time depends on the quantities of enzyme and substrate and, to a minor extent, also on the temperature. At a temperature of 45° C.–55° C., the reaction time is 2–24 hours, preferably 5–8 hours. It is sensible to arrange a relatively short reaction time at higher temperatures, since the enzyme is more readily degraded. The substrate quantity (=quantity of rhamnolipids) which is present in the mixture is maximally 200 g/l, and the enzyme quantity 0.1–50 U/g of rhamnolipids, preferably 1–10 U/g, and particularly preferably 5 U/g, of rhamnolipids.

Following completion of the reaction, the L-rhamnose is isolated from the solution by separating off the fatty phase by means of centrifugation or by decanting until a phase separation has been effected. If necessary, the aqueous phase is subsequently clarified, for example using active charcoal. Clarification is understood to mean the removal of turbidity substances and coloring substances. This step is advisable if an L-rhamnose is to be obtained which is as pure as possible. Subsequently, the aqueous solution is concentrated and the L-rhamnose is crystallized out.

EXAMPLE 1

Cleavage of the rhamnolipids 1 and 3 by naringinase and hesperidinase 10 g of rhamnolipid 1 or 3 are emulsified in 100 ml of ammonium acetate buffer (50 mM, pH 5.5) or double-distilled water and 150 U of naringinase or hesperidinase (from Sigma, Germany) are then added. The reaction is effected at 70° C. while stirring. The values for $V_{max}$ which are achieved under these conditions are summarized in Table 1. Under these conditions, the naringinase cleaves the 10 g of rhamnolipid 3 employed in 4 hours (hesperidinase 7 hours) into 2.5 g of rhamnose (~98% yield) and rhamnolipid 1. The cleavage of rhamnolipid 1 proceeds appreciably more slowly (see Table 1) and incompletely, probably owing to the inactivation of the enzyme over the relatively long period of time.

The reaction was monitored using thin layer chromatography, and the rhamnose was quantitatively determined by means of HPLC.

| TLC: | Eluent: | $CHCl_3/CH_3OH/HAc$ 65:5:2 |
|---|---|---|
| | TLC plate: | Silica gel 60 F254 |
| | Spraying reagent: | $MeOH/HAc/H_2SO_4$ conc./anis-aldehyde 85:10:5:1 |
| | Development: | 5 minutes at 120° C. |

TABLE 1

Enzymic cleavage of rhamnolipid 1 and rhamnolipid 3 by means of hesperidinase and naringinase [the $V_{max}$ values relate to 1 U of α-L-rhamnosidase activity; 1 U is defined as the enzyme quantity which is capable of cleaving 1 μmol of p-nitrophenyl-α-L-rhamnopyranoside per min]:

| Hesperidinase: (Sigma No. H-8137, Penicillium spec.) | |
|---|---|
| "$V_{max}$" rhamnolipid 3: | ~50 μgmin$^{-1}$u$^{-1}$ |
| "$V_{max}$" rhamnolipid 1: | ~0.5 μgmin$^{-1}$u$^{-1}$ |
| Naringinase: (Sigma No. H-1385, Penicillium decumbens) | |
| "$V_{max}$" rhamnolipid 3: | ~80 μgmin$^{-1}$u$^{-1}$ |
| "$V_{max}$" rhamnolipid 1: | ~5.0 μgmin$^{-1}$u$^{-1}$ |
| HPLC: Column: | HPAP (100 × 7.8 mm) Biorad |
| Precolumn: | Carbo P (30 × 4.6) Biorad |
| Temperature: | 85° C. |
| Eluent: | Double-distilled water |
| Flow rate: | 0.4 ml/minute |
| Load | 5 μl |
| Detector: | Differential refractometer (Beckmann) |

The working up of the rhamnose is effected in accordance with the customary methods described in the literature (PCT-EP 91-01426).

EXAMPLE 2

Cleavage of rhamnolipids 1 and 3 by α-L-rhamnosidase from Penicillium sp. DSM 6825 and/or 6826

10 g of rhamnolipid 1 or 3 are emulsified in 100 ml of ammonium acetate buffer (50 mM, pH 5.0) or double-distilled water and 150 U of the enzyme according to the invention are then added. The reaction is effected at 50° C. while stirring. The values for $V_{max}$ which are achieved under these conditions are summarized in Table 2. Under these conditions, the α-L-rhamnosidase according to the invention cleaves the 10 g of rhamnolipid 1 employed in about 5–8 hours (α-L-rhamnosidase from Penicillium sp. DSM 6825: about 8 hours; α-L-rhamnosidase from Penicillium sp. DSM 6826: about 5 hours) into 3.05 g of rhamnose (~94% yield) and the corresponding fatty acid. The cleavage of rhamnolipid 3 proceeds appreciably more slowly (see Table 2) and incompletely, probably likewise owing to the inactivation of the enzyme over the relatively long period of time.

TABLE 2

Enzymic cleavage of the rhamnolipids. The $V_{max}$ values relate to 1 U of α-L-rhamnosidase activity; 1 U is defined as the quantity of enzyme which is able to cleave 1 μmol of p-nitrophenyl-α-L-rhamnopyranoside per minute:

| α-L-Rhamnosidase from Penicillium sp. DSM 6825 | Penicillium sp. DSM 6825 |
|---|---|
| | "$V_{max}$" rhamnolipid 3: ~0.03 μgmin$^{-1}$u$^{-1}$ |
| | "$V_{max}$" rhamnolipid 1: ~40.0 μgmin$^{-1}$u$^{-1}$ |
| α-L-Rhamnosidase from Penicillium sp. DSM 6826 | Penicillium sp. DSM 6826 |
| | "$V_{max}$" rhamnolipid 3: ~0.05 μgmin$^{-1}$u$^{-1}$ |
| | "$V_{max}$" rhamnolipid 1: ~70.0 μgmin$^{-1}$u$^{-1}$ |

The L-rhamnose is once again isolated in accordance with the known methods; in addition, the fatty acid which has been cleaved off can be isolated by extraction under acid conditions.

EXAMPLE 3

Screening for strains which produce α-L-rhamnosidase

Microorganisms were enriched from various soil samples on nutrient media containing the methyl or tert-butyl esters of rhamnolipid 2 as the sole C source using current microbiological methods (Drews, Mikrobiologisches Praktikum (Practical Microbiology), 45–84, Springer Verlag 1983), and pure cultures were isolated. Some 37 of the approximately 400 strains which were isolated were able to degrade rhamnolipids. However, in only some of the strains was it possible to detect significant α-L-rhamnosidase activity; in this context, two strains (Penicillium sp. DSM 6825 and Penicillium sp. DSM 6826) were found to be particularly good producers.

p-Nitrophenyl-α-L-rhamnopyranoside is used as the substrate for detecting the α-L-rhamnosidase activity. 10 mg of this substrate are dissolved in 10 ml of ammonium acetate buffer (pH 5.5, 50 mM). 100 μl of culture filtrate or cell lysates are added to 900 μl of this solution and the mixture is then incubated at 40° C. After 0, 3, 6, 9 and 12 minutes, 200 μl are removed and mixed with 800 μl of 200 mM borate buffer, pH 9. The release-of p-nitrophenol is monitored photometrically at 410 nm; naringinase (following Romero et al. Anal. Biochem. 149 566–571 (1985)) was used as the control.

EXAMPLE 4

Production of the α-L-rhamnosidases using the strains Penicillium sp. DSM 6825 and Penicillium sp. DSM 6826

These strains are first of all streaked out on agar plates containing HA medium (yeast extract 4 g/l, malt extract 10 g/l, glucose 4 g/l, agar 20 g/l, pH 6.0), and the plates are incubated at 25° C. for 10–14 days until good sporulation has been achieved. A spore suspension (50 ml 0.9% NaCl; 0.05% Tween 80) is prepared from two plates which are well grown over and then used for inoculating 10 l of production medium.

The following nutrient solution is used as the production medium: 3 g/l of rhamnolipid 1 or 2, or alkyl esters of the rhamnolipids, or rhamnolipid mixtures (e.g. concentrated filtrate from Pseudomonas aeruginosa culture), 1 g/l $KH_2PO_4$, 0.5 g/l $(NH_4)_2SO_4$, 0.1 g/l $MgSO_4.7H_2O$, 0.1 g/l $CaCl_2$, 0.1 g/l casamino acids, pH 5.5. Cultivation is carried out in a 10 l paddle mixer reactor at 300 rpm and 0.6 vvm, and at 27° C. and a pH of 5.5. The period of cultivation is 5–10 days.

At the end of the fermentation, the cells are separated off by filtration and the culture filtrate is filtered (0.22 μm) to render it sterile. This culture filtrate contains the major portion (over 90%) of the α-L-rhamnosidase activity (5000 U/l) and can be employed either directly or following lyophilization, or concentration by ultrafiltration on a 10 kD membrane, for cleaving the rhamnolipids.

EXAMPLE 5

Isolation and characterization of the α-L-rhamnosidase from Penicillium sp. DSM 6826

A concentrate possessing an activity of 50 U/ml was used as the starting material for the further purification of the α-L-rhamnosidase.

Chromatography on Sepharose Q containing 20 mM Tris/HCl, pH 7.6, is carried out as the first step. Elution is effected using a gradient of 0–0.5M NaCl and the yield which is obtained is in the region of 80%, in association with a purification factor of 5; the enzyme possesses a specific activity of 62 U/mg of protein.

This fraction is subjected to further chromatography on a Mono P column (Pharmacia) (25 mM imidazole/HCl to PBE 74, pH 5.0, 1:12). The α-L-rhamnosidase is eluted at a pH of 5.6–5.8. The yield is in the order of 70%.

Following appropriate rebuffering, the protein is chromatographed on a Superose 12 column (1×30 cm). 100 mM ammonium acetate, pH 5.0, containing 100 mM NaCl is used as the buffer. Monitoring with the aid of SDS gel electrophoresis indicates a protein band in the range from 60–100 kd, depending on the extent to which the enzyme is glycosylated.

The investigations summarized in the table below were carried out using the purified enzyme.

TABLE 3

Influence of different substances on the activity of the α-L-rhamnosidase according to the invention

| Substance | % activity |
|---|---|
| Control | 100 |
| $CaCl_2$ (20 mM) | 127 |
| $MgSO_4$ (2 mM) | 106 |
| KCl (100 mM) | 69 |
| CsCl (2 mM) | 96 |
| $CoCl_2$ (2 mM) | 41 |
| $CuCl_2$ (0.5 mM) | 40 |
| $FeSO_4$ (0.5 mM) | 100 |
| $MnCl_2$ (2 mM) | 27 |
| $ZnCl_2$ (2 mM) | 65 |
| EDTA (10 mM) | 22 |
| EDTA/$CaCl_2$ (10/10 mM) | 90 |
| EGTA (10 mM) | 60 |
| EGTA/$MgSO_4$ (10/10 mM) | 124 |
| L-Rhamnose (0.5 M) | 51 |
| L-Rhamnose (1.0 M) | 39.5 |
| L-Rhamnose (1.5 M) | 26.4 |

EXAMPLE 6

Determination of the N-terminal sequence of the α-L-rhamnosidase from the strain Penicillium sp. DSM 6826, and of naringinase The enzyme from Penicillium sp. DSM 6826, which enzyme was obtained in accordance with Example 5, as well as the naringinase from Penicillium decumbens (crude enzyme, Sigma No. N-1385), which was purified by the same process, are purified again on an acrylamide gel (10%) and, following transfer of the polypeptides by means of electroblotting transferred to a ProBlot® membrane (from Applied Biosystems, Sequencers No. 42, April 1990, (Applied Biosystems). Under these conditions, the naringinase gave rise to a single band whereas the purified enzyme from DSM 6826 could be resolved into two bands which were very closely adjacent to each other. The N-terminal sequences of the three polypeptide chains are determined with the aid of a 477a Peptide Sequencer from Applied Biosystems. The results in Table 4 demonstrate clearly that both the polypeptide chains of the active preparation from strain DSM 6826 are different from naringinase (Sigma No. N-1385).

TABLE 4

| Peptides | N-terminal sequence |
|---|---|
| Naringinase (96 000 D) | A S V P X G E X I L A P S S I E L I P T (SEQ ID NO: 3) |
| α-L-rhamno-sidase 6826, peptide I (96 000 D) | D T N D Q T S A K V D R G T F D D P A A R L (SEQ ID NO: 1) |
| α-L-Rhamno-sidase 6826, peptide II (83 500 D) | F F G S $X_1$ Q S L Y L K L V L K F G T L F D ($X_2$) A (SEQ ID NO: 2) |

$X_1$ denotes probably cysteine
$X_2$ amino acid not determined

We claim:

1. An isolated α-L-rhamnosidase that catalyzes the cleavage of the bond between terminal L-rhamnose and the aglycone of a rhamnose-containing glycoside, said α-L-rhamnosidase having a molecular weight of from 60 to 100 kD and an isoelectric point ascertained by chromatofocussing of from about 5.6 to 5.8.

2. An isolated α-L-rhamnosidase that catalyzes the cleavage of the bond between terminal rhamnose and the aglycone of rhamnose-containing glycosides, having a molecular weight of 60–100 kd, which α-L-rhamnosidase contains the amino-terminal amino add sequence Asp Thr Asn Asp Gln Thr Ser Ala Lys Val Asp Arg Gly Thr Phe
    Asp Asp Pro Ala Ala Arg Leu         (SEQ ID NO: 1)

or

Phe Phe Gly Ser Xaa Gln Ser Leu Tyr Leu Lys Leu Val Leu Lys
    Phe Gly Thr Leu Phe Asp Xaa Ala     (SEQ ID NO:2).

3. The α-L-rhamnosidase as claimed in claim 1, wherein the α-L-rhamnosidase originates from Penicillium sp.

4. The α-L-rhamnosidase as claimed in claim 2, wherein the isoelectric point of the α-L-rhamnosidase, ascertained by chromatofocussing, is 5.6–5.8.

5. The α-L-rhamnosidase as claimed in claim 2, wherein the α-L-rhamnosidase originates from Penicillium sp. DSM 6825, Penicillium sp. DSM 6826, or a mutant of Penicillium sp. DSM 6825 or 6826 that catalyzes the cleavage of the bond between terminal L-rhamnose and the aglycone of a rhamnose-containing glycoside.

6. The α-L-rhamnosidase as claimed in claim 1, wherein the aglycone is a fatty acid.

7. A method for the preparation of L-rhamnose comprising the steps of incubating a rhamnolipid with an α-L-rhamnosidase as claimed in claim 1, and isolating the L-rhamnose.

8. A raw enzyme of α-L-rhamnosidase produced by a process comprising the steps of:

a) fermenting Penicillium sp. DSM 6825, Penicillium sp. DSM 6826, or a mutant of Penicillium sp. DSM 6825 or 6826 that catalyzes the cleavage of the bond between terminal L-rhamnose and the aglycone of a rhamnose-containing glycoside;

b) separating off the biomass from the culture broth; and c) concentrating the culture supernatant.

9. A method for the preparation of L-rhamnose comprising the steps of incubating a rhamnolipid with an α-L-rhamnosidase as claimed in claim 2, and isolating the L-rhamnose.

10. A method for the preparation of L-rhamnose comprising the steps of incubating a rhamnolipid with an α-L-rhamnosidase as claimed in claim 8, and isolating the L-rhamnose.

11. An α-L-rhamnosidase as claimed in claim 3, wherein the α-L-rhamnosidase originates from Penicillium sp. DSM 6825 or a mutant of Penicillium sp. DSM 6825 that catalyzes the cleavage of the bond between terminal L-rhamnose and the aglycone of a rhamnose-containing glycoside.

12. An α-L-rhamnosidase as claimed in claim 3, wherein the α-L-rhamnosidase originates from Penicillium sp. DSM 6826 or a mutant of Penicillium sp. DSM 6826 that catalyzes the cleavage of the bond between terminal L-rhamnose and the aglycone of a rhamnose-containing glycoside.

13. An isolated α-L-rhamnosidase wherein the α-L-rhamnosidase is produced by a process of claim 8 and further comprising the step of isolating the α-L-rhamnosidase from the culture supernatant.

14. A purified α-L-rhamnosidase wherein the α-L-rhamnosidase is produced by a process of claim 8, and further comprises the step of concentrating said α-L-rhamnosidase by ultrafiltration and then lyophilizing said α-L-rhamnosidase.

15. A purified α-L-rhamnosidase of claim 14, wherein the process further comprises the step of purifying said α-L-rhamnosidase by precipitation, anion exchange chromatography, chromatofocussing, HIC chromatography, exclusion chromatography, or affinity chromatography.

16. A purified α-L-rhamnosidase of claim 14, wherein the biomass is separated from the culture broth by filtering and further comprising the steps of ultrafiltrating to concentrate the α-L-rhamnosidase and then conducting anion exchange chromatography, chromatofocussing, and then exclusion chromatography.

* * * * *

UNITED STATES PATENT AND TRADEMARK OFFICE
CERTIFICATE OF CORRECTION

PATENT NO. : 5,641,659
DATED : June 24, 1997
INVENTOR(S) : Johannes MEIWES et al.

It is certified that error appears in the above-indentified patent and that said Letters Patent is hereby corrected as shown below:

In Claim 2, Col. 13, line 34, "add" should read --acid--.

Signed and Sealed this

Second Day of December, 1997

Attest:

BRUCE LEHMAN

*Attesting Officer*    *Commissioner of Patents and Trademarks*